United States Patent [19]

Amor

[11] Patent Number: 6,042,562

[45] Date of Patent: Mar. 28, 2000

[54] HANDLE FOR A CATHETER

[75] Inventor: Max Amor, Nancy, France

[73] Assignee: Medicorp Endovascular Technologies, Inc., Ashburn, Va.

[21] Appl. No.: 09/182,310

[22] Filed: Oct. 30, 1998

[30] Foreign Application Priority Data

Oct. 30, 1997 [FR] France ................................. 97 13636

[51] Int. Cl.⁷ .................................................. A61M 25/00
[52] U.S. Cl. ........................... 604/95; 116/284; 116/309; 604/264
[58] Field of Search ...................... 604/95, 264; 116/284, 116/309

[56] References Cited

U.S. PATENT DOCUMENTS

| | | |
|---|---|---|
| 4,397,091 | 8/1983 | Gustavsson et al. .................... 33/127 |
| 5,309,902 | 5/1994 | Kee et al. ........................... 128/202.27 |
| 5,489,275 | 2/1996 | Thompson et al. ..................... 604/264 |

FOREIGN PATENT DOCUMENTS

| | | |
|---|---|---|
| 0790066 | 2/1992 | European Pat. Off. . |
| WO8803035 | 5/1988 | WIPO . |

*Primary Examiner*—John D. Yasko
*Attorney, Agent, or Firm*—Roylance, Abrams, Berdo & Goodman, L.L.P.

[57] ABSTRACT

A handle for a catheter, comprising a marking arrangement using index markings which can be read through a window. The window is arranged on the handle, and the index markings are carried by an embossed wheel pivoting on an axis perpendicular to the axis of the catheter.

5 Claims, 2 Drawing Sheets

HANDLE FOR A CATHETER

BACKGROUND OF THE INVENTION

1. Technical Field

The invention concerns a handle for a catheter, particularly for a catheter used in electrophysiology.

2. Background of the Invention

A catheter for electrophysiological use customarily comprises a catheter body carrying a juncture at its proximal end and a flexible part at its distal end, on which are arranged a plurality of electrodes which may be annular electrodes. These electrodes are provided to measure the potential, for example, by being applied against the interior wall of the heart or of a blood vessel. The electrodes can also be used for the destruction of certain bodily tissues by electrical ablation or radio-frequency.

At its opposite end from the body of the catheter, the juncture of the catheter comprises an electrical connector to secure the connection between the interior conductors arranged within the catheter and the electrodes, and the exterior conductors terminating on the measuring apparatuses.

To indicate the position of the distal end of the catheter, U.S. Pat. No. 5,489,275 discloses a cylindrical ring arranged on the juncture of the catheter, running coaxial with the catheter, and provided with a window. When the ring is set in rotation, the window is moved displaying index markings, each of which corresponds to an identified position of the distal end of the catheter. Thus, when the catheter has been placed in an identified position, the operator then pivots the ring until the window displays the index marking corresponding to the identified position. The drawback of this coaxial arrangement of a cylindrical ring is due to the variable position of the window, which is not always on the side of the juncture of the catheter which is most visible to the operator.

SUMMARY OF THE INVENTION

One object of the invention is a handle for the catheter to enhance the visibility of a marking index, on the surface of the handle visible in the view of the operator.

In rotatable catheters, a control device allows for the rotation of the distal end of the catheter. This device carries approximate precision graduated markings, aligned with the position of the control device.

Another object of the invention is for a handle for a rotatable catheter, which allows for the display of a marking index for indexing the position of the distal end of the catheter, for example, either its curvature or its angular position.

Still another object of the invention is a handle for a catheter, having a marking system made up of an index to be read through a window, characterized in that the window is arranged on the handle, and the index markings are carried on an embossed wheel pivoting on an axis perpendicular to the axis of the catheter. In this manner, the window or windows are always situated at the same sites in relation to the handle, which facilitates viewing by the operator.

According to other characteristics of the invention:

the handle presents a cutout in which is placed the embossed wheel, the index markings carried by the embossed wheel passing by under the window;

the handle presents a second window and the index markings are carried on the two surfaces of the embossed wheel, to allow for reversibility of the handle;

the embossed wheel is independent of the control of the rotational orientation of the catheter, and the marking system gives position information regarding the distal end of the catheter;

a mechanical connection is provided between the embossed wheel and the control of rotational orientation of the catheter, wherein the marking system gives angular information regarding the distal end of the rotatable part of the catheter in relation to the distal end of the body of the catheter or an indication regarding the curvature of the distal end of the catheter.

Other characteristics arise from the description which follows with reference to the attached drawings in which.

Figure 1:
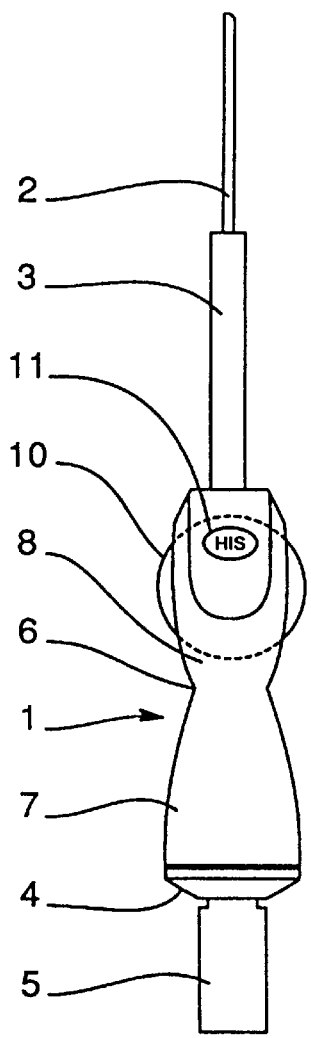
FIG. 1 is a top view of a first embodiment of a handle for a catheter according to the invention.

In FIG. 1, the handle 1 for the catheter is found at the proximal end of a catheter 2. Toward the front of the handle 1 is a sleeve 3 for the protection of the catheter in the vicinity of the handle 1. To the rear of the handle 1 is an electrical connector 4 for connection between the interior conductors within the catheter coming from the electrodes arranged at the distal end of the catheter, and the exterior conductors outside the catheter, the electrical connector 4 lodged in a sheathing 5 and connected to the measuring apparatuses and/or recording apparatuses, for example, an electrocardiogram.

Handle 1 presents a narrow central part 6, and to the rear of the narrow central part, an essentially truncated conical part 7, and in front of the narrow central part a curved and proportional, flattened part 8. This curved and proportional part 8 presents a central cutout 9, shown in FIG. 2, in which is placed an embossed wheel 10 (FIG. 4) and its support 13 (FIG. 3). Embossed wheel 10 is arranged in central cutout 9, and its diameter is greater than the width of the front curved and proportional part 8 of handle 1, so that embossed wheel 10 extends outward laterally on either side of the front part 8 of the handle. Toward the front part 8 of handle 1 is incorporated a window 11, aligned essentially in the axis of the handle, above embossed wheel 10. This window 11 allows for observation of the index markings inscribed on embossed wheel 10, which pass under window 11 when embossed wheel 10 is set in rotation by the operator actuating the handle and acting on the parts of embossed wheel 10 which extend laterally on either side of front part 8 of handle 1.

Figure 2:
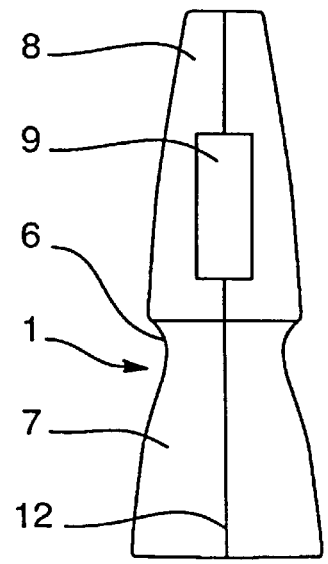
FIG. 2 is a side view of the handle for a catheter of FIG. 1.
Figure 3:
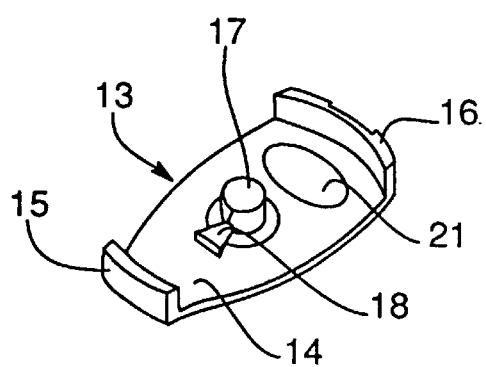
FIG. 3 is a perspective of an embossed wheel support for a handle for a catheter as in FIG. 1.

In FIG. 2, handle 1 appears to be constituted of two halves separated by a median surface 12. The same references designate the same parts as in FIG. 1.

In FIG. 3, support 13 of embossed wheel 10 includes a base 14 and two borders 15 and 16 shaped in arcs of a circle. In the center of base 14 is mounted a pivot 17, and on the base adjacent to pivot 17 is provided a catch or detent 18. Support 13 supporting the embossed wheel is intended to be ratcheted by a click-catch in front part 8 of handle 1 and to receive embossed wheel 10, centered on pivot 17 and pivoting within borders 15, 16 shaped in an arc of a circle.

Figure 4:
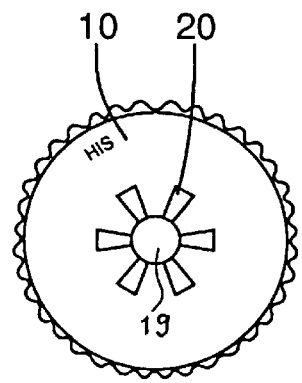
FIG. 4 is a plan view of an embossed wheel for a handle for a catheter as in FIG. 1.

In FIG. 4, embossed wheel 10 is shown as a wheel provided with relief designs around its periphery. It includes a central orifice 19 to receive the pivot 17 of support 13. Around this central orifice 19 and radiating toward the exterior are arranged slots 20 which are intended to cooperate with detent 18 to immobilize embossed wheel 10 in positions corresponding to the presence of the index markings which are viewable under window 11 of handle 1. On the surface of embossed wheel 10, facing the slots 20, are arranged identification index markings indicating for example the position of the distal end of the catheter. One index marking can for example be HIS, to indicate the presence of the distal end of the catheter in the cluster or beam of HIS. The other index markings correspond, for example, to the presence of the distal end of the catheter in the right auricle, in the right ventricle, and so on.

To assure the reversibility of handle 1, each of the two halves of the handle (FIG. 2) may contain a window such as window 11. Support 13 supporting the embossed wheel can also have a window 21 corresponding to window 11 and embossed wheel 10 can carry index markings on its two surfaces.

In the first embodiment, embossed wheel 10, of which the rotation axis is perpendicular to the axis of the catheter in handle 1, is set by the operator to a position to retain a piece of information. The information displayed in this position indicates for example the position of the end of the catheter. This information is useful to the operator, particularly when there are simultaneously several catheters in a heart.

In this first embodiment, the embossed wheel 10 is independent of the control of the rotational orientation of the distal end of the catheter. The position marking system having the embossed wheel 10 and its index markings serves as a reminder to the operator.

Figure 5:
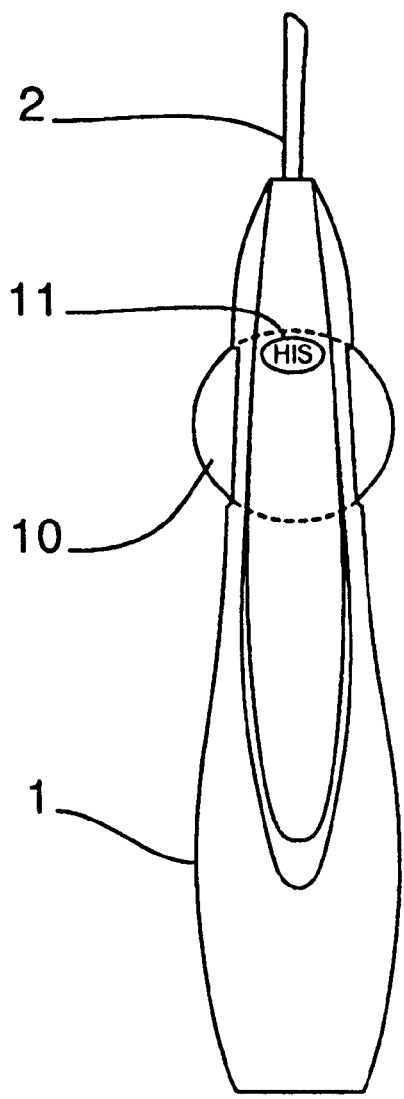
FIG. 5 is a top view of a second embodiment of a handle for a catheter according to the invention.
Figure 6:
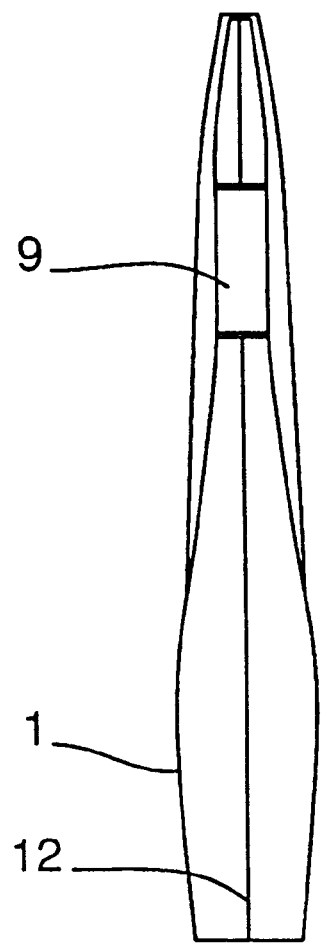
FIG. 6 is a side view of the handle for a catheter as in FIG. 5.

In FIGS. 5 and 6, handle 1 of catheter 2 has a more elongated shape than in FIG. 1. It is however still realized in two halves separated by a median surface 12, and it presents a central cutout 9 toward the front, and a window 11 for observation of the index markings marked on embossed wheel 10.

In the second embodiment, shown in FIGS. 5 and 6, the catheter presents a nonrotatable catheter body or part of the catheter body, and at the distal end of this body, a flexible or rotatable part of the catheter.

The index markings carried by embossed wheel 10 are angular indications corresponding to the rotational orientation of the distal end of the flexible part of the catheter in relation to the distal end of the body of the catheter or indications of the curvature of the distal tube or of the distal part of the catheter.

In this second embodiment, a mechanical connection is provided between embossed wheel 10 and the rotational orientation control means of the distal end of the flexible part of the catheter. With this arrangement, the information furnished by embossed wheel 10 is correlated with the rotational orientation of the distal end of the flexible part of the catheter. This rotational orientation is defined as the angle formed by the tangent at the distal end of the flexible part of the catheter and the tangent at the distal end of the body of the catheter or as the curvature of the distal part of the catheter.

In this manner, handle 1 of the catheter is provided with a marking arrangement indicating the position of the distal end of the catheter. In this arrangement, embossed wheel 10, lodged in handle 1, can pivot about its axis, and is provided with index markings on at least one of its surfaces. These index markings can be signs, symbols, or series of characters comprehensible by the operator. These markings are visible through at least one window on handle 1. When there are two windows in handle 1, they allow simultaneous observation of the two surfaces of the embossed wheel and observation of the same index markings.

The angular position of embossed wheel 10 corresponds to a piece of information which can be used by the operator. The indication, indicia or piece of information can be the site of the heart or of an artery in which the distal end of the catheter is situated. It can also be the angle formed by the tangent at the distal end of the body of the catheter (or nonrotatable part of the catheter) and the tangent at the distal end of the flexible part of the catheter (or rotatable part of the catheter).

What is claimed is:

1. A handle for a catheter, comprising a marking system including index markings which can be read through a window, characterized in that the window is arranged on the handle, having a longitudinal axis and the index markings are carried by an embossed wheel pivoting on an axis perpendicular to said longitudinal axis of the handle.

2. The handle of claim 1, characterized in that the handle contains a cutout in which is situated the embossed wheel, wherein a portion of the index markings carried by the embossed wheel are visible under the window.

3. The handle of claim 2, characterized in that the handle contains a second window and the index markings are carried on both a first and second surface of the embossed wheel, to ensure the reversibility of the handle.

4. The handle of claim 2, characterized in that the embossed wheel is independent of the control of the rotational orientation of the catheter and the marking arrangement provides information regarding the position of a distal end of the catheter.

5. The handle of claim 2, characterized in that a mechanical connection is provided between the embossed wheel and the control of the rotational orientation of the catheter, and the marking system provides angular information regarding a distal end of a rotatable part of the catheter in relation to a distal end of the body of the catheter or an indication of curvature of the distal end of the catheter.

* * * * *